United States Patent
Arts et al.

(10) Patent No.: US 8,303,581 B2
(45) Date of Patent: Nov. 6, 2012

(54) CATHETER WITH REMOTELY EXTENDIBLE INSTRUMENTS

(75) Inventors: Gene H. Arts, Berthoud, CO (US);
Timothy J. Bahney, Portland, OR (US);
John D. Carlton, Las Vegas, NV (US);
Duane E. Kerr, Berthoud, CO (US);
William Nau, Longmont, CO (US)

(73) Assignee: Covidien LP, Mansfield, MA (US)

( * ) Notice: Subject to any disclaimer, the term of this patent is extended or adjusted under 35 U.S.C. 154(b) by 804 days.

(21) Appl. No.: 12/202,546

(22) Filed: Sep. 2, 2008

(65) Prior Publication Data

US 2010/0057078 A1 Mar. 4, 2010

(51) Int. Cl.
*A61B 18/14* (2006.01)

(52) U.S. Cl. .......................................... 606/41; 606/34

(58) Field of Classification Search .................. 600/106, 600/127, 136, 139, 153; 606/110, 113, 114, 606/46, 34
See application file for complete search history.

(56) References Cited

U.S. PATENT DOCUMENTS

| | | |
|---|---|---|
| 4,846,171 A | 7/1989 | Kauphusman et al. |
| 5,342,393 A | 8/1994 | Stack |
| 5,413,571 A | 5/1995 | Katsaros et al. |
| 5,529,067 A | 6/1996 | Larsen et al. |
| 5,540,715 A | 7/1996 | Katsaros et al. |
| 5,582,617 A | 12/1996 | Klieman et al. |
| 5,630,833 A | 5/1997 | Katsaros et al. |
| 5,649,959 A | 7/1997 | Hannam et al. |
| 5,817,119 A | 10/1998 | Klieman et al. |
| 5,846,248 A * | 12/1998 | Chu et al. ...................... 606/114 |
| 6,066,139 A | 5/2000 | Ryan et al. |
| 6,099,550 A | 8/2000 | Yoon |
| 6,221,039 B1 | 4/2001 | Durgin et al. |
| 6,773,409 B2 | 8/2004 | Truckai et al. |
| 6,786,905 B2 | 9/2004 | Swanson et al. |
| 7,179,255 B2 | 2/2007 | Lettice et al. |
| 7,318,823 B2 | 1/2008 | Sharps et al. |
| 2004/0073238 A1 | 4/2004 | Makower |
| 2005/0096502 A1* | 5/2005 | Khalili .......................... 600/106 |
| 2006/0253126 A1 | 11/2006 | Bjerken et al. |
| 2006/0258955 A1* | 11/2006 | Hoffman et al. .............. 600/564 |
| 2009/0259105 A1* | 10/2009 | Miyano et al. ................ 600/127 |

* cited by examiner

*Primary Examiner* — Michael Peffley
*Assistant Examiner* — Thomas Giuliani

(57) ABSTRACT

An electrosurgical apparatus for performing a surgical procedure includes a housing having an elongated flexible shaft with proximal and distal ends. The shaft having a plurality of tubes disposed therein that define a corresponding plurality of working channels configured to house a corresponding plurality of surgical instruments. An actuator is dimensioned for selective reciprocation within the shaft and configured to operably engage one or more of the corresponding plurality of surgical instruments and deploy the corresponding surgical instrument to an operating cavity as needed during a surgical procedure.

12 Claims, 5 Drawing Sheets

CATHETER WITH REMOTELY EXTENDIBLE INSTRUMENTS

TECHNICAL FIELD

The present disclosure relates to devices for use with catheters, endoscopes and other electrosurgical instruments for coagulating tissue. More particularly, the present disclosure relates to a catheter having a series of channels disposed therein for housing a variety of selectively extendible and deployable surgical instruments.

BACKGROUND OF RELATED ART

This present disclosure relates to instruments and methods for performing minimally invasive, laparoscopic or endoscopic surgical procedures. More particularly, the present disclosure relates to instruments and methods that are especially suitable for procedures that require or benefit from minimally invasive access to anatomical conduits, vessels or tissue for treating the same.

Over the last several years, minimally invasive or endoscopic surgical tools and methods have been developed for treating vessels and tissue that are less intrusive and less traumatic. For example, with one known technique, the surgeon makes a few small incisions in the abdomen and inserts one or more elongated surgical instruments, e.g., forceps, scissors, clip appliers, staplers, etc., into the incision and carefully manipulates the instruments while viewing the operating area through an endoscope or laparoscope. These techniques are often referred to as endoscopic, laparoscopic, minimally invasive, or video-assisted surgery. References to endoscopic surgery and endoscopes below is intended to encompass all these fields, and the exemplary operations described below with reference to endoscopes can also be accomplished with laparoscopes, gastroscopes, and any other imaging devices which may be conveniently used.

Typically, many of the above-described techniques require the surgeon to insert different instruments through the working lumen of the catheter to treat tissue, separate vessels or perform other surgical procedures. As can be appreciated, this simply adds to the overall complexity of the operation since it requires the repeated exchange of surgical instruments through the working lumen to perform the different tasks associated with a given surgical procedure.

SUMMARY

The present disclosure relates to an electrosurgical apparatus for performing a surgical procedure including a housing having an elongated shaft with proximal and distal ends. The shaft includes a plurality of tubes disposed therein that define a corresponding plurality of working channels configured to house a corresponding plurality of surgical instruments. An actuator is included and dimensioned for selective reciprocation within the shaft and configured to operably engage one or more of the corresponding plurality of surgical instruments and deploy the surgical instrument to an operating cavity as needed during a surgical procedure. The actuator is configured to allow remote operation of the surgical instrument within the operating cavity.

In one embodiment, the plurality of surgical instruments are arranged in an array-like manner within the working channels of the shaft. In another embodiment, the plurality of surgical instruments is selected from a group consisting of: vessel sealers, coagulators, biopsy instruments, needles, probes, sensors, graspers, forceps, knives, scissors, sutures, balloon dissectors, stents, irrigators, suction devices, stabilizers, blunt dissectors, lasers, optical devices, implants and anchors.

In yet another embodiment, the actuator includes an actuating cable and/or an electrical cable operably connected thereto. One or more of the cables are utilized to engage, deploy and/or operate one or more of the plurality of surgical instruments.

The housing is adapted to connect to an electrosurgical generator, an irrigation source, a suction source and/or accessory equipment configured to operably connect to at least one of the plurality of surgical instruments. The electrosurgical generator, irrigation source, suction source and/or accessory equipment may be configured to include a controller disposed thereon for remotely controlling the actuator and/or a sensor disposed thereon for indexing the plurality of surgical instruments attached to the flexible shaft.

The present disclosure also relates to an electrosurgical apparatus for performing a surgical procedure having a housing with an elongated flexible shaft attached thereto with proximal and distal ends and a working end including a plurality of tubes disposed therein that define a corresponding plurality of working channels configured to house a corresponding plurality of surgical instruments. The working end is selectively engageable with the distal end of the elongated shaft. An actuator is included that is dimensioned for selective reciprocation within the shaft and configured to operably engage the corresponding plurality of surgical instruments and deploy one or more of the corresponding plurality of surgical instruments to an operating cavity as needed during a surgical procedure. A sensor may be disposed on the housing for indexing (from each of the working ends) the plurality of surgical instruments attached to the flexible shaft.

The present disclosure also relates to a method for performing a surgical procedure and includes the steps of: providing a housing and attaching a flexible, elongated shaft with distal and proximal ends to the housing; engaging one or more working ends (in series) to the distal end of the housing, the working end including a plurality of tubes disposed therein that define a corresponding plurality of working channels for housing a corresponding plurality of surgical instruments; and controlling an actuator to engage one or more of the corresponding plurality of surgical instruments and deploy the corresponding surgical instrument(s) to an operating cavity as needed for use during a surgical procedure.

The method may also include the steps of indexing the plurality of surgical instruments disposed in the working end(s); and providing feedback to the surgeon relating to the status and/or location ("stored", "deployed", "in use", "disposed" and/or "malfunction") of each of the plurality of surgical instruments.

DETAILED DESCRIPTION

Figure 1:
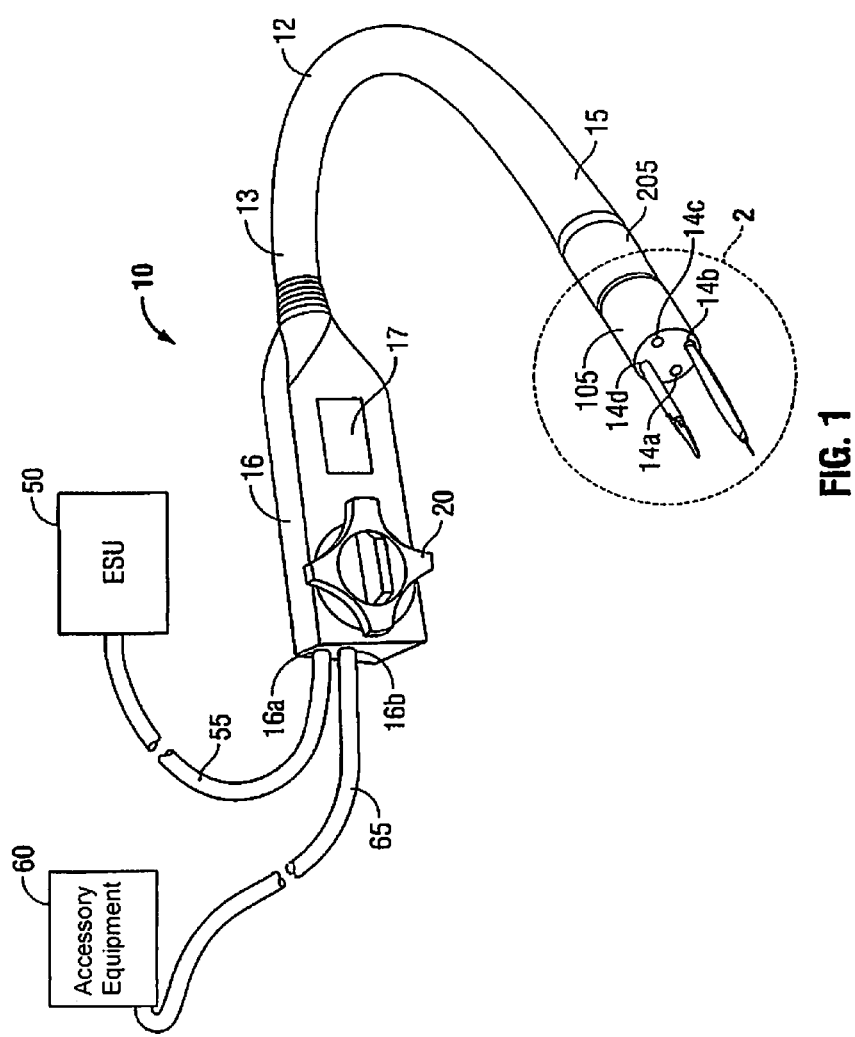
FIG. 1 is a front, perspective view of electrosurgical instruments shown extending through working channels of a flexible shaft of a catheter in accordance with one embodiment of the present disclosure.

Referring now to FIG. 1, a multi-port catheter, generally identified by reference numeral 10 is shown. Catheter 10 includes a proximal end 13, a distal end 15 and an elongated shaft 12 disposed therebetween. In the drawings and in the description that follows, the term "proximal", as is traditional, will refer to the end of the forceps that is closer to the user, while the term "distal" will refer to the end of the forceps that is further from the user.

The proximal end 13 of catheter is operably engaged to a housing 16 that, in turn, operably connects to an electrosurgical generator 50 and accessory equipment 60 via cables 55 and 65, respectively. Accessory equipment 60 is configured to support one or more of the various features associated with the surgical instruments attached to catheter 10 as explained in more detail below, e.g., suction, irrigation, gas supply, optical equipment, steering and actuating handles and/or act as an alternate energy source for supporting instruments with alternate energy capabilities, e.g., microwave, ultrasound, laser, etc.

Figure 2:
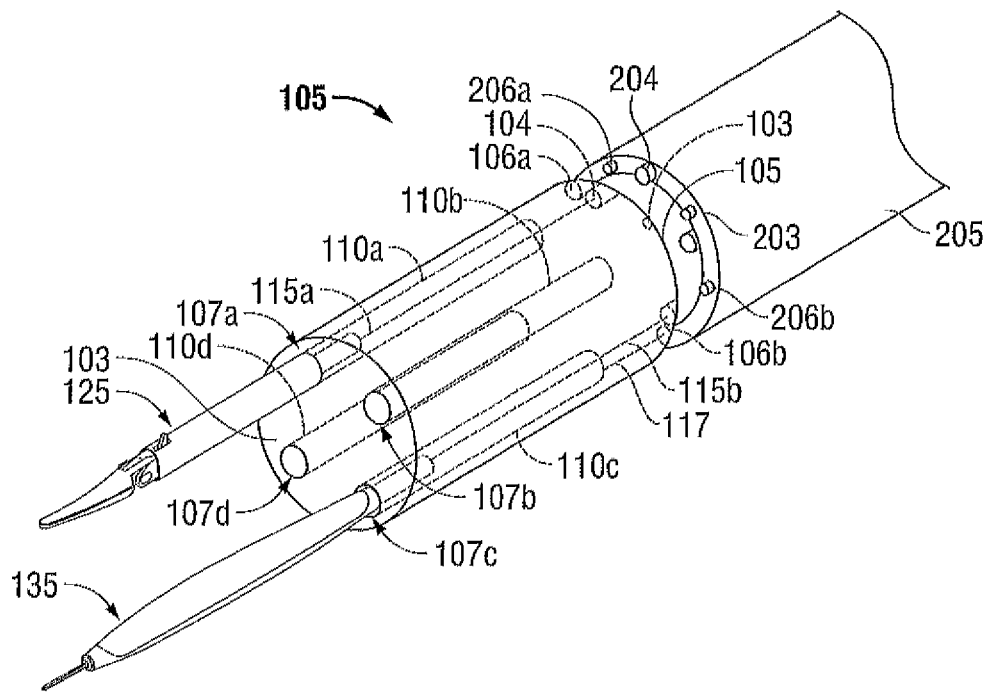
FIG. 2 is a schematically-illustrated, enlarged, side perspective view of one embodiment of the present disclosure showing a working end for use with the elongated shaft having selectively extendable instruments disposed therein.
Figure 3:
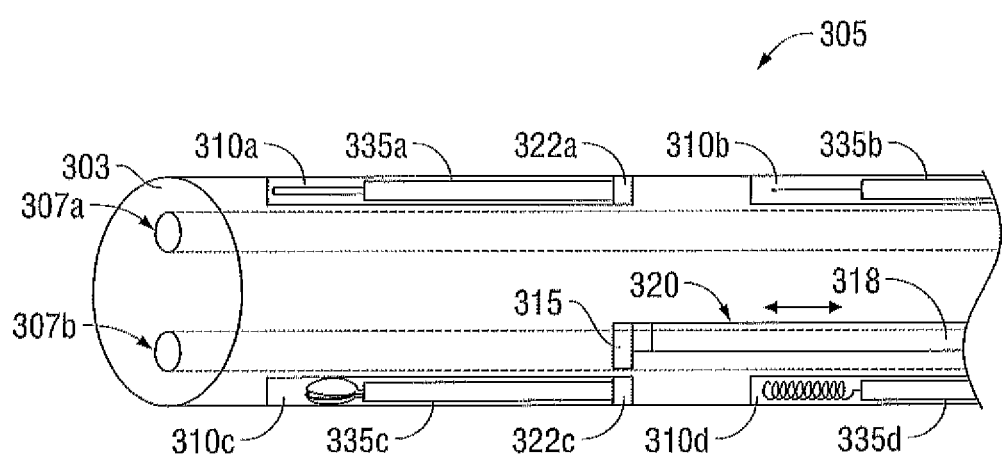
FIG. 3 is a schematically-illustrated, internal view of the present disclosure showing various selectively extendible instruments disposed therein and a deployment tool.

As shown in FIGS. 1-3, shaft 12 is generally elongated and flexible to facilitate negotiating various cavities and other internal structures of an operating cavity and includes a plurality of working channels 14a-14d defined in a general, array-like manner therein and that extend therethrough. The shaft 12 may be rigid in an alternative embodiment. Housing 16 may include a similar plurality of channels 16a and 16b defined therein that align in registration with one or more respective channels 14a-14d defined in shaft 12 to facilitate remotely controlling one or more surgical instruments. Alternatively, one or more deployment actuators or tools 320 may be utilized to control the various surgical instruments, as explained in detail below. Housing 16 may also include one or more instrument controllers 20 disposed thereon that are actuatable to control (activate, rotate, extend, operate, articulate, etc.) one or more surgical instruments or the deployment tool 320.

Turning now to FIG. 2 which shows one embodiment of the catheter 10 having four tubes 110a-110d disposed therein that define four channels 107a-107d for housing a corresponding number of surgical instruments, e.g., instruments 125 and 135. More particularly, the distal end 15 of shaft 12 is configured to operatively engage one or more working ends 205 and 105 that are, in turn, configured to house one or more surgical instruments, e.g., surgical instruments 125 and 135, therein. As shown, working end 205 is configured to removeably engage distal end 15 or may be configured to be integrally associated therewith. Working end 205, in turn, includes a plurality of mechanical interfaces 203, 204, 206a and 206b that are dimensioned to operably engage a corresponding plurality of interfaces 103, 104, 106a and 106b disposed on working end 105.

The mechanically engaging interfaces, namely, interfaces, 203, 204, 206a and 206b on end 205 and the mechanically engaging interfaces 103, 104, 106a and 106b on end 105 are configured to assure accurate and consistent alignment of the internal working channels 110a-110d, mechanical actuators 115a, 115b and internal electrical connections 117. As such, the various electrical and mechanical connections of working end 105 are universal and allow selective replacement (or interchangeability) of different working ends onto working end 205 as needed. A surgeon can select a working end 105 containing specific surgical tools needed for a particular surgical procedure and engage the working end 105 onto end 205, thereby reducing the need to feed a new surgical instrument down the channel of the catheter 10 for each use. Alternatively, a surgeon may manually load working end 105 with specific instruments needed for a particular surgical procedure or order a custom set of instruments that is loaded by a manufacturer.

As explained in more detail below with respect to the operation of the catheter 10, the surgeon has the ability to rotate the working end 105 independently (or with shaft 12) to orient a new surgical instrument, e.g., instrument 125, for use inside a operating cavity as needed without compromising the integrity of the operating cavity and without having to replace instruments during a surgical procedure due to sterilization or mechanical issues. Moreover, each instrument, e.g., instrument 125, may be rotated into place and deployed (via controllers 20 and actuators 115a and 115b) either separately or in tandem as needed. Certain channels, e.g., channels 107b and 107d, may be left available in case a new or unanticipated instrument is needed during a given procedure.

For example, the working end 105 may include a vessel sealing device 125 and an electrosurgical pencil 135, which are each independently deployable, activatable and controllable via one or more controllers 20 disposed on the housing 16 or as part of the accessory equipment 60. Vessel sealer 125 is configured to allow a surgeon to selectively and remotely grasp, dissect, manipulate, seal and/or cut vessels and tissue. Electrosurgical pencil 135 allows a surgeon to remotely coagulate and cut vessels and tissue. When not in use, each instrument, e.g., sealer 125, is housed within a corresponding channel or pocket 110a disposed in working end 105. A remote actuator, e.g., actuator 115a, is activated to deploy the vessel sealer 125 from the distal end 103 of the working end 105.

Actuator 115a may be multifunctional and include one or more cables or other electrical connections that enable the surgeon to deploy, rotate, articulate, extend and otherwise operate the surgical instrument during use thereof. Similarly, electrical connections 117 may be multifunctional as well and allow the surgeon to activate various electrical components of the surgical instrument as well as actuate various electrically-controlled operating components (motors, solenoids, gears, etc.).

Other instruments may be selected as part of a given working end 105 that perform different functions depending upon the particular surgery involved. Examples of instruments that may be utilized within the various working channels include vessel sealing instruments e.g., as described in commonly-owned U.S. application Ser. No. 11/348,072, electrosurgical pencils, e.g., as described in commonly-owned U.S. application Ser. No. 11/337,990 and ablation instruments, e.g., as described in commonly-owned U.S. application Ser. No. 11/236,400. Other instruments and devices that may be utilized include: biopsy instruments, needles, probes, sensors, graspers, forceps, knives, scissors, sutures, stents, irrigators, balloon dissectors, suction devices, stabilizers, blunt dissectors, lasers, optical devices, implants, anchors, tissue ablators, etc. These instruments may be housed within the articulating members of the end of the shaft 12.

FIG. 3 shows another embodiment of a working end 305 for use with catheter 10 that includes two internally disposed channels 307a and 307b defined therein for use in deploying various surgical instruments 335a-335d. Channels 307a and 307b are generally offset relative to one another and extend through the distal end 303 of working end 305, thereby allowing independent and/or simultaneous deployment of surgical instruments 335a-335d to the operating cavity. Working end 305 also includes a plurality of elongated cavities 310a-310d disposed around the internal peripheral surface thereof that are dimensioned to house one or more instruments therein. Similar to the working ends 105 and 205 above, working end 305 may be configured to house various surgical instruments needed for a particular surgical procedure, thereby reducing the need to feed a new surgical instrument down the channels 307a, 307b of the catheter 10 for each use.

Working end 305 also includes a deployment tool 320 that operably connects to one or more controllers on the housing 16 that is configured to allow selective deployment and control of a particular surgical instrument into a respective working channel, e.g., 307a, and into the operating cavity. More particularly, deployment tool 320 includes a shaft 318 that is selectively reciprocateable within the catheter 10 to allow a surgeon the ability to selectively engage a desired surgical instrument, e.g., instrument 335c, from the surgical instrument's respective cavity 310c and deploy the instrument 335c into the operating cavity via a working channel 307a or 307b. The deployment tool 320 may include a universal coupling 315 disposed at a distal end thereof that is configured to engage a corresponding coupling 322a, 322c disposed on the surgical instrument 335a, 335c, respectively. The universal coupling 315 may be multifunctional and include one or more actuators, cables or electrical connections that enable the surgeon to engage, deploy, rotate, articulate, extend and otherwise operate the surgical instrument (or components thereof, e.g., various electrically-controlled operating components (motors, solenoids, gears, etc.)) during use.

In the particular embodiment shown in FIG. 3, the various tools include an electrosurgical pencil 335a, a needle electrode 335b, a biopsy tool 335c and a deployable stent 335d. Again, other instruments may also be housed within the various cavities of working end 305 including: probes, sensors, graspers, forceps, knives, scissors, sutures, irrigators, suction devices, stabilizers, dissectors, lasers, optical devices, implants, anchors, tissue ablators, etc.

The remote proximal end 13 of the catheter shaft 12, the housing 16 or the accessory equipment 60 may include one or more sensors or indexing devices 17 that are configured to locate, orient or "index" the various surgical instruments disposed within working end 305 and, e.g., the cavity location and/or particular function of each instrument. For example, the housing 16 (or equipment 60) may include a senor or an indexing tool (or other visual indicator) 17 that corresponds to both instrument type and instrument location within the working end 305. The surgeon may then manually engage a desired surgical instrument (or activate an automatic instrument engagement protocol) based on the indexing information displayed on the housing 16 (or equipment 60). Moreover, it is contemplated that a second set of cavities (not shown) may be defined within the working end 305 for "used" instruments, sample specimens or additional working components (e.g., additional stents).

Sensors 17 may also be used to confirm engagement/disengagement of the proper instrument, mechanical failure, or various operating characteristics of the surgical instruments as needed during use, impedance matching, temperature monitoring, etc. Various tissue parameters may also be determined by the sensor(s) 17, e.g., tissue impedance, tissue temperature, tissue moisture, etc.

Figure 4A:
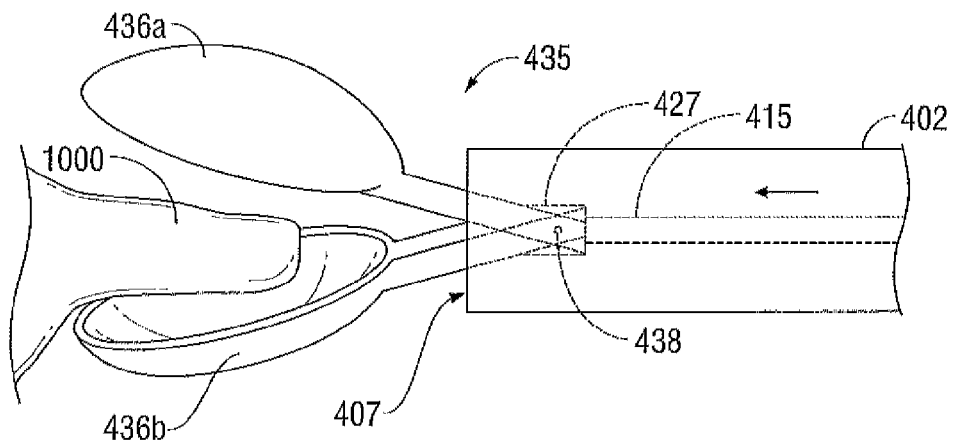
FIGS. 4A-4C are schematically-illustrated, greatly enlarged, sequential views of a biopsy tool for use with the catheter of FIG. 1.
Figure 4B:
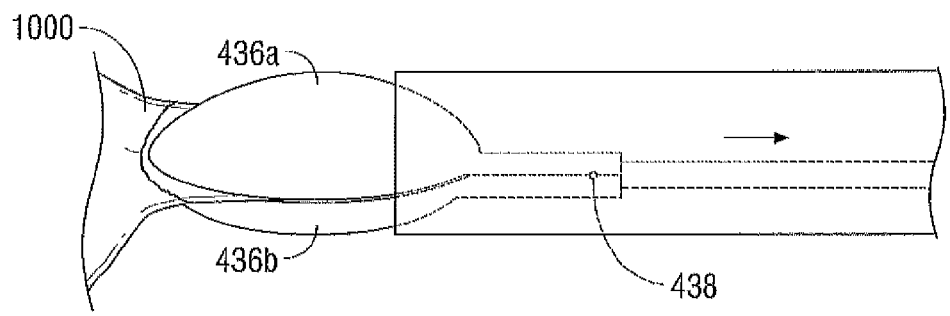
Figure 4C:
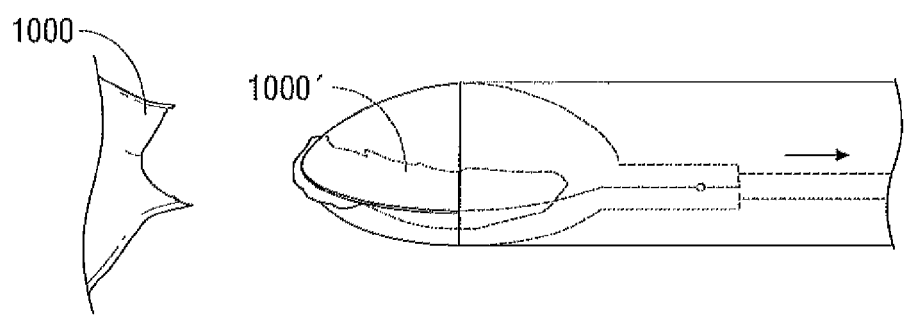

FIGS. 4A-4C shows an example of a surgical instrument or tool 435 that may be selectively deployable from one or more of the hereindescribed working ends for use with catheter 10. More particularly, and similar to the instruments described above, instrument 435 is a biopsy tool configured to fit within working channel 407 defined in tube 402. A tool actuator 415 is reciprocateable within the working channel 407 and allows a surgeon to remotely operate the biopsy tool 435 as needed. For example, the biopsy instrument 435 is initially deployed by moving the actuator 415 distally past the end of working channel 407 which opens a pair of cup-like opposing jaws 436a and 436b of the biopsy tool 435 about a pivot 438 via a spring bias 427 disposed at the proximal end of the tool 435. Once the opposing jaws 436a and 436b are opened, the biopsy tool 435 may be moved into position to engage specimen tissue 1000 as shown in FIG. 4A.

Once positioned, the surgeon pulls the actuating tool proximally (while maintaining shaft 12 in place), which forces the opposing jaws 436a and 436b to close about the tissue specimen 1000 as shown in FIG. 4B. The edges of the opposing jaw members 436a and 436b include sharpened edges that allow the jaw members 436a and 436b to cut and capture the tissue specimen 1000 between the jaw members 436a and 436b. Once the tissue 1000 is cut, the surgeon continues to pull the tool 435 proximally so that the tissue specimen 1000' may be safely stored between the opposing jaw members 436a and 436b within working channel 507 (See FIG. 4C).

Figure 5:
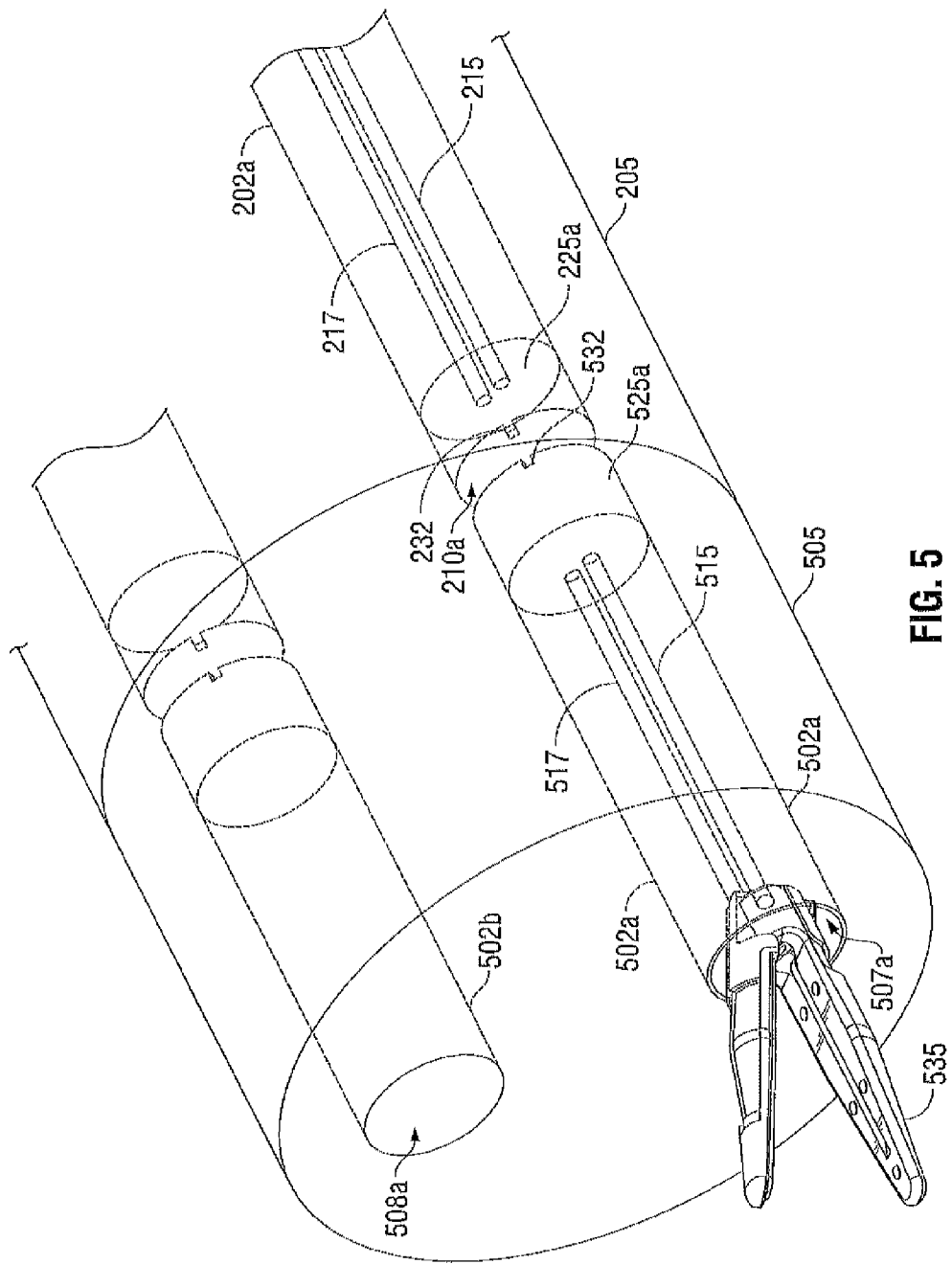
FIG. 5 is a schematically-illustrated, enlarged view showing an exchangeable instrument magazine for use with the catheter of FIG. 1.

FIG. 5 shows another embodiment of a working end 505 for use with catheter 10 that includes one or more internally disposed tubes 502a and 502b having channels 507a and 508a defined therein for use in deploying various surgical instruments, e.g., instrument 535 within channel 507a. More particularly, working end 505 is selectively engageable with end 205 of catheter 10 in a similar manner described above with respect to FIG. 2. In the instance wherein the actuating and electrical cables need to be properly aligned to operate a particular surgical instrument, it is necessary to ensure proper alignment of the working channels 507a and 210a of ends 505 and 205, respectively.

For example, in order to ensure actuating cables 515 and 215 align for proper operation of instrument 535, the proximal end 525a of tube 502a may be configured to align with the distal end 225a of tube 202a. One or more alignment interfaces 532 and 232 may be employed on ends 525a and 225a, respectively. The alignment interfaces 532 and 232 may also be employed to register the electrical cables 517 and 217 on each end 525a and 225a. Ideally, the mechanical interfaces 532a and 232a are universal connections or interfaces, thereby allowing interchangeability of various working ends of surgical instrumentation with differently configured or "loaded" configurations of surgical tools. The mechanical interfaces 532a and 232a may be threaded, snap-fit, tongue and groove or any other suitable type of mating connectable interfaces.

Figure 6:
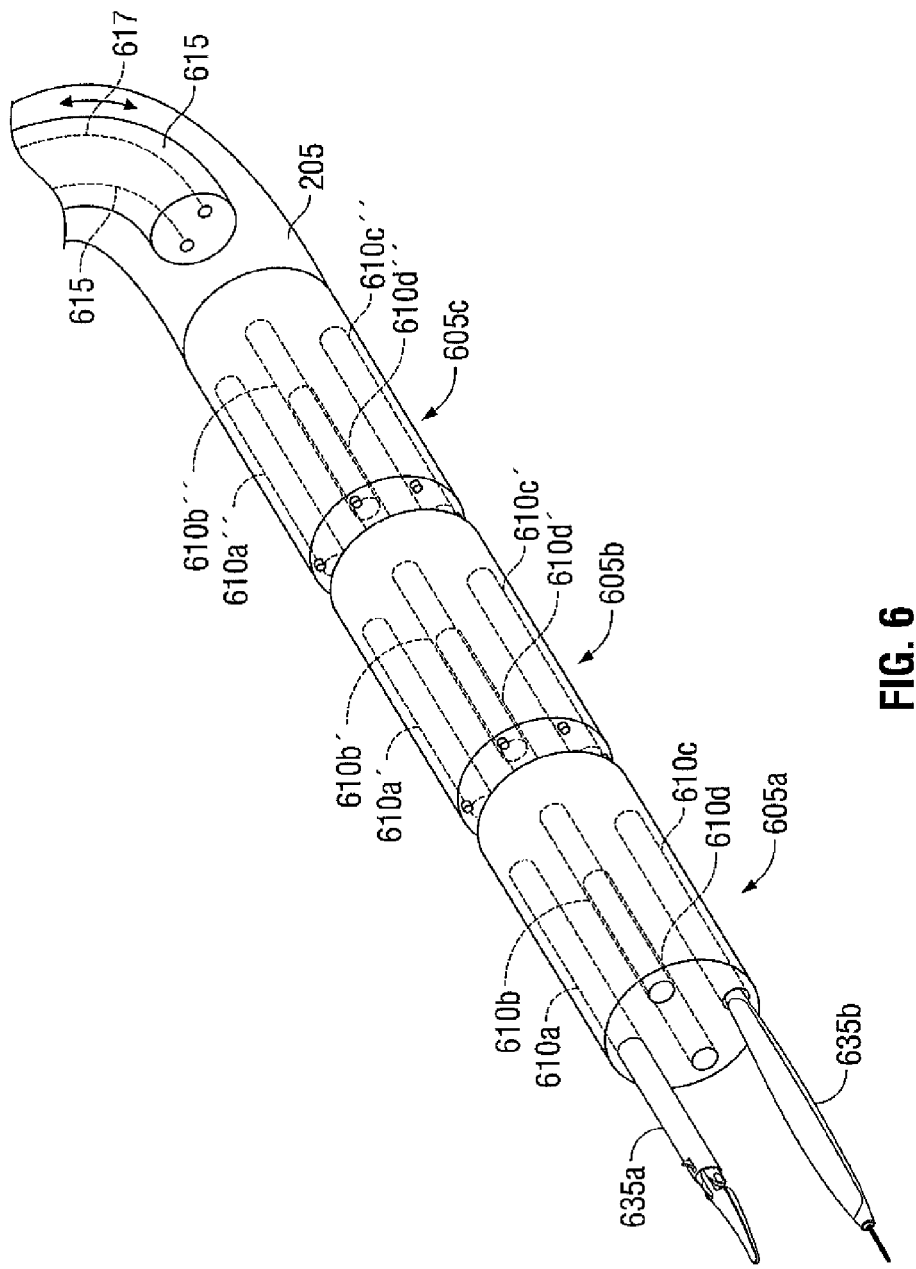
FIG. 6 is a schematically-illustrated, enlarged view showing a series of exchangeable magazines for use with the catheter of FIG. 1.

FIG. 6 shows another embodiment of a catheter 10 that includes a series of interchangeable working ends 605a-605c that may be selectively engaged to end 205 of catheter 10. Each interchangeable working end 605a-605c includes a plurality of cavities 610a-610d, 610a'-610d' and 610a"-610d" defined therein for housing various surgical instruments. One or more mechanical interfaces (similar to the mechanical interfaces 532 and 232 described above) may be employed to align and/or secure the plurality of working ends 605a-605c to one another and/or to end 205. A deployment tool 615 may be utilized to remotely engage, deploy and/or operate any one of the instruments, e.g., instruments 635a, 635b, within the operating cavity as needed. For example, in the particular arrangement shown in FIG. 6, as many as twelve instruments may be used within a surgical cavity without having to remove and insert instrumentation in a conventional manner. One or more actuating cables 615 and electrical connections 617 may be employed to permit remote engagement, deployment and operation of the various surgical instrumentation as needed.

The present disclosure also relates to a method for performing a surgical procedure and includes the steps of: providing a housing and attaching a flexible, elongated shaft with distal and proximal ends to the housing. The method also includes the additional steps of: engaging one or more working ends (in series) to the distal end of the housing, the working end including a plurality of tubes disposed therein that define a corresponding plurality of working channels for housing a corresponding plurality of surgical instruments, and controlling an actuator to engage one or more of the corresponding plurality of surgical instruments and deploy the corresponding surgical instrument to an operating cavity as needed for use during a surgical procedure.

The method may also include the steps of indexing the plurality of surgical instruments disposed in the working end(s), and providing feedback to the surgeon relating to the status and/or location of each of the plurality of surgical instruments. The feedback relating to the status and/or location of each of the plurality of surgical instruments may include indicia displayed on the housing such as: "stored", "deployed", "in use", "disposed" and/or "malfunction".

From the foregoing and with reference to the various figure drawings, those skilled in the art will appreciate that certain modifications can also be made to the present disclosure without departing from the scope of the present disclosure. For example and as mentioned above, the housing, generator, suction/irrigation equipment and/or the accessory equipment may include a sensor or indexing mechanism or tool which orients and "indexes" the various surgical instruments, before, during or after use. The indexing tool may be configured to provide real-time feedback to the surgeon as to the status and location of each instrument. As a new instrument or magazine of instruments is added or interchanged, the indexing tool automatically (or manually) updates the display or index on the appropriate system component (e.g., housing, generator, suction/irrigation equipment and/or the accessory equipment) thereby providing accurate information to the surgeon.

Moreover, there have been described and illustrated herein several embodiments of a catheter with various working ends for treating tissue and performing other surgical procedures. While particular embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An apparatus for performing a surgical procedure, comprising:
    a plurality of surgical instruments;
    a housing having an elongated shaft with proximal and distal ends;
    a working end selectively engageable with the distal end of the elongated shaft, including a plurality of tubes disposed therein that define a plurality of working channels configured to house the plurality of surgical instruments; and
    an actuator dimensioned for selective reciprocation within the working end,
    wherein rotation of the working end with respect to a longitudinal axis of the elongated shaft engages one of the plurality of surgical instruments with the actuator to deploy the surgical instrument to an operating cavity as needed during a surgical procedure.

2. An apparatus for performing a surgical procedure according to claim 1, wherein the actuator is configured to allow remote operation of the at least one surgical instrument within the operating cavity.

3. An apparatus for performing a surgical procedure according to claim 1, wherein the plurality of surgical instruments is arranged in an array-like manner within the working channels of the working end.

4. An apparatus for performing a surgical procedure according to claim 1, wherein the plurality of surgical instruments is selected from a group consisting of: vessel sealers, coagulators, biopsy instruments, needles, probes, sensors, graspers, forceps, knives, scissors, sutures, stents, irrigators, balloon dissectors, suction devices, stabilizers, blunt dissectors, lasers, optical devices, implants tissue ablators and anchors.

5. An apparatus for performing a surgical procedure according to claim 1, wherein the actuator includes at least one of an actuating cable and an electrical cable operably connected thereto configured to at least one of engage, deploy and operate one of the plurality of surgical instruments.

6. An apparatus for performing a surgical procedure according to claim 1, wherein the housing is adapted to connect to at least one of an energy source, an irrigation source, a suction source and accessory equipment configured to operably connect to at least one of the plurality of surgical instruments.

7. An apparatus for performing a surgical procedure according to claim 6, wherein at least one of the housing, energy source, irrigation source, suction source and accessory equipment is configured to include a controller disposed thereon for remotely controlling the actuator.

8. An apparatus for performing a surgical procedure according to claim 6, wherein at least one of the housing, energy source, irrigation source, suction source and accessory equipment is configured to include a sensor disposed thereon for indexing the plurality of surgical instruments in the working end.

9. An apparatus for performing a surgical procedure, comprising:
    a plurality of surgical instruments;
    a housing having an elongated flexible shaft with proximal and distal ends;
    a working end including a plurality of tubes disposed therein that define a plurality of working channels configured to house the plurality of surgical instruments, the working end being selectively engageable with the distal end of the elongated shaft; and
    an actuator dimensioned for selective reciprocation within the working end,
    wherein rotation of the working end with respect to a longitudinal axis of the elongated shaft engages at least one of the plurality of surgical instruments with the actuator to deploy the at least one surgical instrument to an operating cavity as needed during a surgical procedure.

10. An apparatus for performing a surgical procedure according to claim 9, wherein the actuator is configured to allow remote operation of the at least one surgical instrument within the operating cavity.

11. An apparatus for performing a surgical procedure according to claim 9, wherein a plurality of working ends having a plurality of surgical instruments are attached to the elongated shaft in series.

12. An apparatus for performing a surgical procedure according to claim 11, wherein the housing is configured to include a sensor disposed thereon for indexing the plurality of surgical instruments attached to the flexible shaft from each of the working ends.

* * * * *